United States Patent
Bierbaum et al.

(10) Patent No.: US 11,053,533 B2
(45) Date of Patent: Jul. 6, 2021

(54) **IDENTIFICATION OF METHICILLIN RESISTANT *STAPHYLOCOCCUS AUREUS* (MRSA)**

(71) Applicant: Bruker Daltonik GmbH, Bremen (DE)

(72) Inventors: Gabriele Bierbaum, Bonn (DE); Christiane Szekat, Wachtberg (DE); Nahed Alsabti, Sankt Augustin (DE); Michaele Josten, Bonn (DE); Marion Reif, Bonn (DE)

( * ) Notice: Subject to any disclaimer, the term of this patent is extended or adjusted under 35 U.S.C. 154(b) by 678 days.

(21) Appl. No.: 15/107,133

(22) PCT Filed: Dec. 18, 2014

(86) PCT No.: PCT/EP2014/078470
§ 371 (c)(1),
(2) Date: Jun. 22, 2016

(87) PCT Pub. No.: WO2015/097061
PCT Pub. Date: Jul. 2, 2015

(65) Prior Publication Data
US 2016/0355865 A1    Dec. 8, 2016

Related U.S. Application Data

(60) Provisional application No. 61/920,054, filed on Dec. 23, 2013.

(51) Int. Cl.
*C12Q 1/14* (2006.01)
*G01N 33/68* (2006.01)

(52) U.S. Cl.
CPC ........... *C12Q 1/14* (2013.01); *G01N 33/6851* (2013.01); *G01N 2333/31* (2013.01); *G01N 2800/44* (2013.01)

(58) Field of Classification Search
CPC .. C12Q 1/14; G01N 33/6851; G01N 2800/44; G01N 2333/31
See application file for complete search history.

(56) References Cited

FOREIGN PATENT DOCUMENTS

WO    2008154101 A1    12/2008

OTHER PUBLICATIONS

Chatterjee, SS et al. Distribution and regulation of the mobile genetic element-encoded phenol-soluble modulin PSM-mec in methicillin-resistant *Staphylococcus aureus*. PLoS One. Dec. 2011. 6(12): e28781. 6 pages. (Year: 2011).*
Gagnaire, J et al. Detection of *Staphylococcus aureus* delta-toxin production by whole-cell MALDI-TOF mass spectrometry. PLoS One. Jul. 2012. 7(7): e40660. 9 pages. (Year: 2012).*
Wunschel, SC et al. Bacterial analysis by MALDI-TOF mass spectrometry: an inter-library comparison. J. Am. Soc. Mass Spectrom. 2005. 16: 456-462. (Year: 2005).*
Josten, M et al. Analysis of the matrix-assisted laser desorption ionization-time of flight mass spectrum of *Staphylococcus aureus* identifies mutations that allow differentiation of the main clonal lineages. Journal of Clinical Microbiology. Jun. 2013. 51(6): 1809-1817. First published Apr. 3, 2013. (Year: 2013).*
Kaito, C et al. Transcription and translation products of the cytolysin gene psm-mec on the mobile genetic element SCCmec regulate *Staphylococcus aureus* virulence. PLoS Pathogens. 2011.7(2): e1001267. (Year: 2011).*
Clark, AE et al. Matrix-assisted laser desorption ionization-time of flight mass spectrometry: a fundamental shift in the routine practice of clinical microbiology. Clinical Microbiology Reviews. Jul. 2013. 26(3): 547-603. (Year: 2013).*
Du Z. et al., Identification of *Staphylococcus aureus* and determination of its methicillin resistance by matrix-assisted laser desorption/ ionization time-of-flight mass spectrometry, Analytical Chemistry, American Chemical Society, vol. 74, No. 21, Nov. 1, 2002, pp. 5487-5491.
Lu et al., Peptide Biomarker Discovery for Identification of Methicillin-Resistant and Vancomycin-Intermediate *Staphylococcus aureus* Strains by MALDI-TOF, Analytical Chemistry, vol. 84, No. 13, Jul. 3, 2012, pp. 5685-5692.
Wang et al., Identification of novel cytolytic peptides as key virulence determinants for community-associated MRSA, Nature Medicine, vol. 13, No. 12, Nov. 11, 2007, pp. 1510-1514.
Edwards-Jones et al., Rapid discrimination between methicillin-sensitive and methicillin-resistant *Staphylococcus aureus* by intact cell mass spectrometry, Journal of Medical Microbiology, Society for General Microbiology, vol. 49, No. 3, Mar. 1, 2000, pp. 295-300.
Majcherczyk et al., The discriminatory power of MALDI-TOF mass spectrometry to differentiate between isogenic eicoplanin-susceptible and teicoplanin-resistant strains of methicillin-resistant *Staphylococcus aureus*, FEMS Microbiology Letters, Wiley-Blackwell Publishing LTD, vol. 255, No. 2, Feb. 1, 2006, pp. 233-239.
Josten et al., Identification of agr-positive methicillin-resistant *Staphyloccocus aureus* harbouring the class A mec complex by MALDI-TOF mass spectrometry, International Journal of Medical Microbiology, vol. 304, No. 8, Nov. 1, 2014, pp. 1018-1023.
Wei Sheng Yan Jiu et al., Fenxi Ceshi Xuebao [Journal of Hygiene Research], 2011, vol. 40, No. 3, p. 375-378.
Fenxi Ceshi Xuebao [Journal of instrumental analysis], 2003, vol. 22, No. 1, p. 62-67.

* cited by examiner

*Primary Examiner* — David W Berke-Schlessel
*Assistant Examiner* — Susan E. Fernandez
(74) *Attorney, Agent, or Firm* — Benoit & Côté Inc.

(57) ABSTRACT

The invention provides a method for identifying methicillin resistant *Staphylococcus aureus* (MRSA) in a bacterial sample comprising the steps: classifying bacteria in the sample as *Staphylococcus aureus* (SA) and determining the presence or absence of the phenol soluble modulin peptide or a variant thereof wherein the presence of the PSM-mec peptide or variant thereof indicates methicillin resistant *Staphylococcus aureus*. The variant is preferably the formylated version of the PSM-mec peptide having a mass to charge ratio of 2415 in a singly protonated state.

7 Claims, 2 Drawing Sheets

IDENTIFICATION OF METHICILLIN RESISTANT *STAPHYLOCOCCUS AUREUS* (MRSA)

FIELD OF THE INVENTION

The invention relates to the identification of methicillin resistant *Staphylococcus aureus* (MRSA), in particular by mass spectrometry.

BACKGROUND OF THE INVENTION

*Staphylococcus aureus* (*S. aureus*) is a bacterium of order Bacillales and family Staphylococcaceae that is frequently found in the human respiratory tract and on the skin. Although *S. aureus* is not always pathogenic, it is a common cause of skin infections (e.g. boils), respiratory disease (e.g. sinusitis), and food poisoning. It has demonstrated an exceptional capacity to acquire resistance to antibacterial agents. Methicillin resistant *S. aureus* (MRSA) started to spread in the hospitals in the late 1980s and later community acquired strains (CA-MRSA) followed. It is still one of the five most common causes of hospital-acquired infections and is often the cause of postsurgical wound infections. Today MRSA pose a problem for hospital hygiene in most countries of the world.

The resistance to methicillin is mediated via the mec operon, part of the staphylococcal cassette chromosome mec (SCCmec). Resistance is conferred by the mecA gene, which codes for altered penicillin-binding proteins (e.g. PBP2a) that have a lower affinity for binding β-lactams (penicillins, cephalosporins, and carbapenems). This enables transpeptidase activity in the presence of beta-lactams, preventing them from inhibiting cell wall synthesis. So far, eleven different types of SCCmec with several subtypes and variants have been detected. These cassettes show a high diversity in sequence and integrated mobile elements.

In clinical laboratories, matrix-assisted laser desorption/ionization time of flight mass spectrometry (MALDI TOF MS) of intact cells is increasingly used for the identification of bacteria from patient samples. Analyte ions, in particular ribosomal protein ions, utilized for identifying bacteria by MALDI-TOF MS are usually singly charged, thus one can simply refer to the mass m of the ions. However, the more accurate term is the "charge-related mass" m/z which is actually necessary in mass spectrometry.

Several studies have analyzed the potential of mass spectrometry (in particular MALDI TOF MS) to differentiate methicillin sensitive (susceptible) *S. aureus* (MSSA) from MRSA:

Edwards-Jones V et al., J. Med. Microbiol., 2000, 49, 295-300: "Rapid discrimination between methicillin-sensitive and methicillin-resistant *Staphylococcus aureus* by intact cell mass spectrometry"

Du Z. et al., Anal. Chem., 2002, 74, 5487-5491: "Identification of *Staphylococcus aureus* and determination of its methicillin resistance by matrix-assisted laser desorption/ionization time-of-flight mass spectrometry."

Lu J J. Et al., Anal. Chem., 2012, 84, 5685-5692: "Peptide biomarker discovery for identification of methicillin-resistant and vancomycin-intermediate *Staphylococcus aureus* strains by MALDI-TOF"

Bernardo K. et al., Proteomics, 2002, 2, 747-753: "Identification and discrimination of *Staphylococcus aureus* strains using matrix-assisted laser desorption/ionization-time of flight mass spectrometry"

Majcherczyk P A et al., FEMS Microbiol. Lett, 2006, 255, 233-239: "The discriminatory power of MALDI-TOF mass spectrometry to differentiate between isogenic teicoplanin-susceptible and teicoplanin-resistant strains of methicillin resistant *Staphylococcus aureus*."

Sun et al., Wei Sheng Yan Jiu, 2011, 40, 375-378: "Rapid method study of methicillin-resistant *Staphylococcus aureus* identified by matrix-assisted laser desorption ionization-time of flight mass spectrometry"

SUMMARY OF THE INVENTION

The invention provides a method for identifying methicillin resistant *Staphylococcus aureus* (MRSA) in a bacterial sample comprising the steps: classifying bacteria in the sample as *Staphylococcus aureus* (SA) and determining the presence or absence of the phenol soluble modulin peptide or a variant thereof wherein the presence of the PSM-mec peptide or variant thereof indicates methicillin resistant *Staphylococcus aureus*. The variant is preferably the formylated version of the PSM-mec peptide having a mass to charge ratio of 2415 in a singly protonated state.

The presence of the PSM-mec peptide or variant thereof can be determined by acquiring a mass spectrum of whole (intact) bacteria cells and by determining the presence of at least one mass signal in the mass spectrum with m/z between 2404 and 2420, in particular by the presence of a mass signal centered at m/z of 2415. The presence of the PSM-mec peptide or variant thereof can also be determined by applying a solvent (e.g. an organic solvent like ethanol) to the bacterial sample, acquiring a mass spectrum of the resulting supernatant, and determining the presence of at least one mass signal in the mass spectrum with m/z between 2404 and 2420, in particular by the presence of a mass signal centered at m/z of 2415. Furthermore, the presence of the PSM-mec peptide or variant thereof can be determined by tandem mass spectrometry of the bacterial sample comprising the selection of a parent ions with m/z between 2404 and 2420, in particular by parent ions centered at m/z of 2415.

The bacteria are preferably classified to be *Staphylococcus aureus* by acquiring a sample mass spectrum of the bacteria and comparing the sample mass spectrum with reference mass spectra of a library comprising at least one reference mass spectrum of *Staphylococcus aureus*. The reference mass spectra can be measured mass spectra of well know bacterial strains or can be derived from genetic sequences of bacterial strains. The sample mass spectrum is preferably a MALDI time of flight mass spectrum of whole (intact) bacteria cells. The assignment of bacteria to taxonomic classes (taxonomic classification/identification) using mass spectrometry is well known from publications of van Bar (FEMS Microbiology Reviews, 24, 2000, 193-219: "Characterization of bacteria by matrix-assisted laser desorption/ionization and electrospray mass spectrometry") and Jarman et al. (Analytical Chemistry, 72(6), 2002, 1217-1223: "An Algorithm for Automated Bacterial Identification Using Matrix-Assisted Laser Desorption/Ionization. Mass Spectrometry"). The presence of the PSM-mec peptide or variant thereof is preferably determined by the presence of at least one mass signal in the sample mass spectrum with m/z between 2404 and 2420, in particular by the presence of a mass signal centered at m/z of 2415, wherein the sample mass spectrum is also used for the taxonomic classification, The method according to the present invention may further comprise the step of determining the status of the agr (accessory gene regulator) system of *Staphylococcus aureus*, i.e., whether the *Staphylococcus aureus* are agr positive or agr negative. The presence of the agr system and the presence of the PSM-mec peptide or variant thereof indicate a methicillin resistant *Staphylococcus aureus*, whereas the presence of the agr system and the absence of the PSM-mec peptide or variant thereof indicate a methicillin susceptible *Staphylococcus aureus*. The status of the agr system can be determined by the presence or absence of delta-toxin wherein the presence of the delta-toxin indicates the presence of the agr system (agr positive). The delta toxin can be determined by mass spectrometry wherein the presence of a mass signal in a mass spectrum of the bacterial sample (most preferably the sample mass spectrum utilized for the taxonomic identification) centered at m/z 3007 or m/z 3037 indicates the presence of the delta toxin and thus agr positive *Staphylococcus aureus*. In case of an agr negative status, the *Staphylococcus aureus* are assigned to be undetermined with regard to MRSA and MSSA.

The bacterial sample can stem from cultivation on an agar plate, in a nutrient broth or blood culture or directly from a smear or a body fluid. The bacteria can be collected from colonies grown on the gelatinous culture medium of the agar plate. Bacteria cultivated in the liquid nutrient broth or blood culture can be separated by centrifugation or filtration. In the latter case, preferably after the blood cells have been destroyed prior to the separation. Destroying non-bacterial cells may also be necessary for other samples, like smear and blood.

In order to further confirm the presence of methicillin resistant *Staphylococcus aureus*, an additional antibiotic susceptibility test (AST) can be performed after determining the presence of the PSM-mec peptide or variant thereof. The additional antibiotic susceptibility test can be a conventional test wherein the bacterial growth is determined in a nutrient broth or on a agar plate under the influence of an antibiotic, for example by an optical measurement of the turbidity in the nutrient broth or the growth zone on the agar plate. Other antibiotic susceptibility tests can be based on mass spectrometry and are described for example in U.S. Pat. No. 8,293,496 B2 (Goverun et al.: "Mass spectrometric measurement of microbial resistances") and European Patent Applications No. 13002450.8 (K. Sparbier et al.: "Mass spectrometric determination of microbial resistances") and 13002699.0 (K. Sparbier et al.: "Determining the bacterial resistance by mass spectrometric measurement of the bacterial growth").

In commercial instruments, matrix assisted laser desorption and ionization time-of-flight (MALDI-TOF) mass spectrometer in linear mode are well-established in the practice of mass spectrometric identification of microorganisms, like bacteria. However, in addition to ionization by matrix-assisted laser desorption, other types of ionization are also suitable for acquiring mass spectra according to the invention, e.g. electrospray ionization (ESI) or desorption methods with subsequent chemical ionization (CI). Moreover, different types of mass analyzers can be used, e.g. time-of-flight mass spectrometers with orthogonal ion injection, ion trap mass spectrometers or quadrupole filters. In particular quadrupole filter instruments can be used to determine the presence or absence of mass signals at m/z of 2415, e.g. by selective reaction monitoring.

The presence the phenol soluble modulin peptide (PSM-mec) or a variant thereof can be also determined quantitatively using mass spectrometer like MALDI-TOF MS or quadrupole filter instruments, in particular using calibration substances. In case that PSM-mec peptide is determined quantitatively and the initial concentration of bacteria in the bacterial sample is known, the strength of the resistance can be determined from the determined amount of PSM-mec peptide.

DETAILED DESCRIPTION OF THE INVENTION

Mass Spectrometric Classification of Bacteria

Figure 1:
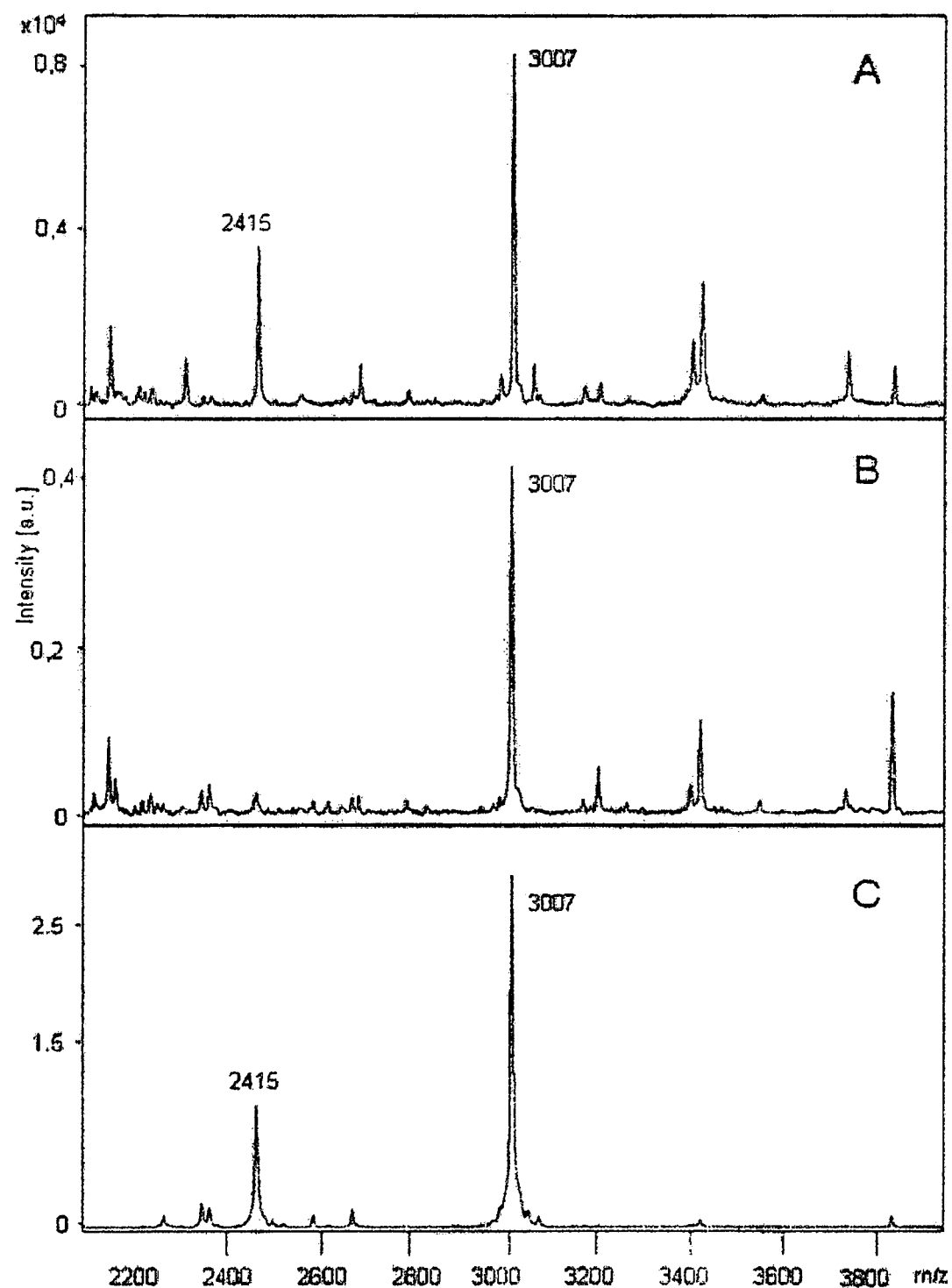
FIG. 1 shows measured MALDI TOF mass spectra of the *Staphylococcus aureus* strain USA100 and a clone of this strain in which the expression of PSM-mec can be down regulated via expression of antisense RNA.

The taxonomic classification of bacteria by mass spectrometry commonly starts with a cultivation of clearly separated colonies (isolates) on a gelatinous culture medium in a Petri-dish. With a small swab, e.g. a wooden toothpick, a tiny amount of bacteria from the colony is spotted onto a mass spectrometric sample plate. The cells are lysed in a well-known way, a solution of matrix material is added and dried, and the sample plate is inserted into the ion source of a time-of-flight mass spectrometer (TOF) operated with ionization by matrix-assisted laser desorption (MALDI). Ions are generated by pulsed laser shots, and their flight time is measured. Usually hundreds of single spectra are added together to improve the signal-to noise ratio. The terms "mass spectrum of a bacteria" or "sample mass spectrum" acquired by a MALDI TOF mass spectrometer usually refers to the sum spectrum, added together from many single mass spectra.

The identification of bacteria by mass spectrometry is presented in some detail in the review article of van Baar (FEMS Microbiology Reviews, 24, 2000, 193-219: "Characterization of bacteria by matrix-assisted laser desorption/ionization and electrospray mass spectrometry"). The identification is for example performed by similarity analyses between a mass spectrum of a bacterial sample and measured reference mass spectra of well-known bacterial strains stored in a library. For each similarity comparison with a reference mass spectrum, a similarity value is calculated. A bacterium may be regarded as identified if the similarity value for a distinct reference mass spectrum shows a clearly better similarity than the similarity values for all other reference spectra, and, in addition, a better value than a preselected similarity threshold. The identification as taxonomic classification is most often possible down to the species level, depending on the number of representative reference mass spectra for the respective species. In a publication by Jarman et al. (Analytical Chemistry, 72(6), 2002, 1217-1223: "An Algorithm for Automated Bacterial Identification Using Matrix-Assisted Laser Desorption/Ionization Mass Spectrometry") computer-assisted methods for automated generation of reference mass spectra and also for similarity analysis between a mass spectrum of a sample under investigation and the automatically generated reference mass spectra are reported.

Identification of the Bacterial Compound Measured at m/z 2415

Several studies have analyzed the potential of MALDI-TOF MS to differentiate methicillin sensitive *Staphylococcus aurcus* (MSSA) from MRSA. In particular, a comparison of an MRSA strain to its isogenic MSSA mutant, that lost SCCmec during storage, shows that there were no differences in the spectra of cell extracts, indicating that the protein encoded by mecA, PBP2a or other resistant variants, is too large (76 kDa) or present in too low amounts to be detected by MALDI-TOF MS of cell extracts during routine measurements.

Using intact MRSA and MSSA cells, i.e. whole cells that are directly deposited on the target without prior extraction, a mass signal at m/z 2415 in MRSA strains of the Rhine-Hesse clone (sequence type (ST) 225, clonal complex (CC) 5) is detected. The mass signal at m/z 2145 is not observed in cell extracts of these strains. The mass signal corresponds to the calculated mass of the singly charged (protonated) ion of the formylated version of the phenol soluble modulin (PSM) PSM-mec.

In order to prove that the mass signal at m/z 2415 is caused by the PSM-mec peptide, a clone is constructed in which expression of PSM-mec can be down regulated via expression of antisense RNA. Therefore, the oligo nucleotides psmmec for (aattcgcctgaatgcaagtatgattaaat-caataatgcttgtaataacaccagtt) and psmmecrev (ctagaactggtgtt-attacaagcattattgatttaatcaagacttgcattcaggcg) are annealed to each other and ligated directly into the EcoRI/XbaI digested vector pEPSA5 yielding pEPSA5-psm-mec. The resulting clone contains a 50 by fragment of psm-mec, located in antisense direction behind a xylose inducible promoter. The plasmid is transformed into an ST5 USA100 isolate (NRS382) which contains the class A mec gene complex. The clone is grown on LB agar containing 34 mg/l chloramphenicol as selective agent in the presence and absence of 50 mM xylose overnight. The cell material is directly deposited on a MALDI-TOF MS ground steel target plate, creating a confluent layer of bacteria. In a next step, 1 µl of formic acid (70%) was added to the bacterial layer, followed by 1 µl of acetonitrile, mixed carefully and air dried. Subsequently, each sample is overlaid with 2 µl of matrix (saturated solution of α-cyano-4-hydroxy-cinnamic acid in 50% acetonitrile/2.5% trifluoroacetic acid) and air dried at room temperature again. The samples are analyzed using a MALDI-TOF MS and measured in the positive linear mode.

FIG. 1 shows a measured spectra of the strain USA100 (FIG. 1A), the strain USA100 harboring pEPSA5-psm-mec in the presence of xylose (FIG. 1B) and the strain USA100 harboring pEPSA5-psm-mec in the absence of xylose (FIG. 1C). The mass signal at m/z 3007 is caused by the delta toxin, and the mass signal at m/z 2415, which corresponds to the PSM-mec peptide, is suppressed by the antisense RNA expressed in the presence of xylose. The results show that the signal at m/z 2415 is strongly decreased after addition of xylose to the clone harboring the recombinant pEPSA5 vector, which proves that the signal observed with this method at m/z 2415 is indeed PSM-mec.

Identification of MRSA with a Class A Mec Gene Complex

PSM-mec is a small excreted peptide which is encoded on three SCCmec cassettes (type II, III and VIII) containing the class A mec gene complex (Chatterjee et al.: "Distribution and regulation of the mobile genetic element-encoded phenol-soluble modulin PSM-mec in methicillin-resistant *Staphylococcus aureus*", 2011, PLoS One, 6:e28781). The production of all PSMs is regulated by the agr system which is involved in quorum sensing in *Staphylococcus aureus* and regulates the expression of delta-toxin and the PSMs directly via the phosphorylated form of AgrA. Therefore, the agr status of a strain can be judged from expression of the delta-toxin (m/z 3007 (most CCs), or m/z 3037 in CC1 strains), which often represents the strongest signal in the spectra of whole cells. The agr negative type strains like *S. aureus* Mu50 do not show production of delta-toxin and PSM-mec and likewise production of PSM-mec is not observed in delta-toxin-negative type strains or in clinical isolates.

However, the class A mec gene complex occurs in several hospital associated MRSA lineages, e.g., the ST5 SCCmec type II hospital associated MRSA in the USA, East Asia and Europe (New York/Japan clone or USA100) and the closely related ST225 SCCmec type II MRSA. ST225 strains are endemic in the hospitals of Central Europe and have represented more than 70% of the MRSA isolates in our region in the last years. Furthermore this group includes the ST239 SCCmec type III strains prevalent in Australia, Asia, the Americas and Eastern Europe (Brazilian/Hungarian clone) and the ST36 SCCmec type II MRSA represented by the EMRSA-16 (USA200), which are isolated in Europe, Australia and the USA as well as the ST45 strain USA600.

TABLE 1

Strains tested

| belonging to the following clonal complexes | Total | harboring a type II or type III SCCmec | harboring a type I, IV, V or X1 SCCmec or MSSA |
|---|---|---|---|
| Extraction on target agr positive strains | | | |
| CC5 MRSA | 68 | 67 | 1 |
| CC8 MRSA | 21 | | 21 |
| CC22 MRSA | 20 | | 20 |
| CC45 MRSA | 8 | | 8 |
| CC30 MRSA | 4 | 2 | 2 |
| CC398 MRSA | 11 | | 11 |
| ST239 | 3 | 3 | |
| other MRSA | 2 | | 2 |
| MSSA | 47 | | 47 |
| in total | 184 | 72 | 112 |
| agr-negative strains | 24 | | |
| total number of strains | 208 | | |

| belonging to the following clonal complexes | | harboring a type II or type III SCCmec | harboring a type I, IV or XI SCCmec or MSSA |
|---|---|---|---|
| Smeared samples agr-positive strains | | | |
| CC5 MRSA | 40 | 40 | |
| CC8 MRSA | 2 | | 2 |
| CC22 MRSA | 11 | | 11 |
| CC45 MRSA | 8 | | 8 |
| CC30 MRSA | 5 | 3 | 2 |
| ST239 | 3 | 3 | |
| MSSA | 40 | | 40 |
| in total | 109 | 46 | 63 |
| agr-negative strains | 15 | | |
| total number of strains | 124 | | |

In further experiments, the presence of PSM-mec is tested in a collection of type strains and well characterized routine clinical MRSA and MSSA isolates (Table 1). Strains are grouped according to their clonal complex (CC). In case of doubt with regard to the presence of the class A mec gene complex, a SCCmec cassette typing is performed by multiplex PCR. In case of unexpected negative or positive measurements, the presence of PSM-mec has also been tested by PCR in order to confirm that SCCmec or parts of SCCmec have not been lost during cryo-preservation or to exclude that the peptide might be present in MSSA.

Two different methods for preparing the MALDI samples are used: Either whole fresh colonies were smeared onto the target plate and overlaid directly with the MALDI matrix, or the cells were extracted with formic acid/acetonitrile directly after deposition on the target as described above.

As described above, agr negative type strains do not show production of delta-toxin and PSM-mec and likewise production of PSM-mcc in not observed in delta-toxin-negative type strains or in clinical isolates. Therefore, all profiles which did not show the delta-toxin signal are excluded from the evaluation in Table 2 (12% of the smeared and 11.5% of extracted samples).

TABLE 2

Sensitivity and specificity of the detection of PSM-mec by MALDI-TOF MS in agr-positive MRSA strains that harbor a class A mec gene complex

| Method | Peak detection window m/z | Sensitivity | Specificity |
|---|---|---|---|
| Extraction on target | 2404-2420 | 0.944 | 0.955 |
|  | 2411-2419 | 0.944 | 1 |
| Smeared samples | 2404-2420 | 0.955 | 0.796 |
|  | 2411-2419 | 0.955 | 1 |

In a first type of evaluation, all signal regardless of intensity, that appear between m/z 2404 and 2420, are included resulting in an overall sensitivity of 0.94 and specificity of about 0.96 using the extraction on the target. When the samples are directly overlaid with the matrix after deposition on the target, the sensitivity is slightly higher, but the specificity of the measurements is lower than 0.8. False positive strains (psm-mec PCR negative) show a weak signal at a slightly lower mass (m/z≤2411).

In a second type of evaluation, all relatively weak signals (e.g. intensity <100 arbitrary units) with an m/z value ≤2411 are excluded and all relatively strong signals (e.g. intensity >100 arbitrary units) at m/z ≥2411 are counted as positive. Thereby, the specificity is considerably increased since all false positive strains are eliminated (Table 2), indicating that psm-mec occurs only in association with SCCmec in the utilized strain collection. The detection of false negative strains is probably caused by low expression of the PSM-mec peptide.

The evaluation of blinded experiments (135 samples for the "extraction on the target" method and 60 samples that are directly smeared onto the target) comprising mainly CC5 MRSA that harbor a type II SCCmec cassette (ST5, ST225) mixed with MRSA of other CCs (CC22, CC8, CC398) as well as 10 MSSA strains, which have been found indistinguishable from the CC5 MRSA in an earlier study employing cell extracts, show that 95% of all agr-positive CC5 MRSA are identified.

The experimental results show that it is possible to identify agr-positive MRSA that harbor a class A mec gene complex by MALDI-TOF MS. In contrast to earlier attempts towards the identification of MRSA via cluster analysis, the PSM-mec peptide is used as specific marker according to the present invention. The identity of marker is known and it is encoded on several SCCmec cassettes. Due to its anionic nature and presence on the surface of the cells, the peptide is detected during whole cell measurements and probably lost from the cell surface when the cells are washed with ethanol which is the first step in the conventional preparation of cell extracts. The class A mec gene complex occurs in several hospital associated MRSA lineages. However, the CA-MRSA strain USA300, livestock associated MRSA or hospital associated CC22 strains (e. g. EMRSA-15), that harbor an SCCmec type IV cassette, cannot be distinguished from MSSA by this method.

Figure 2:
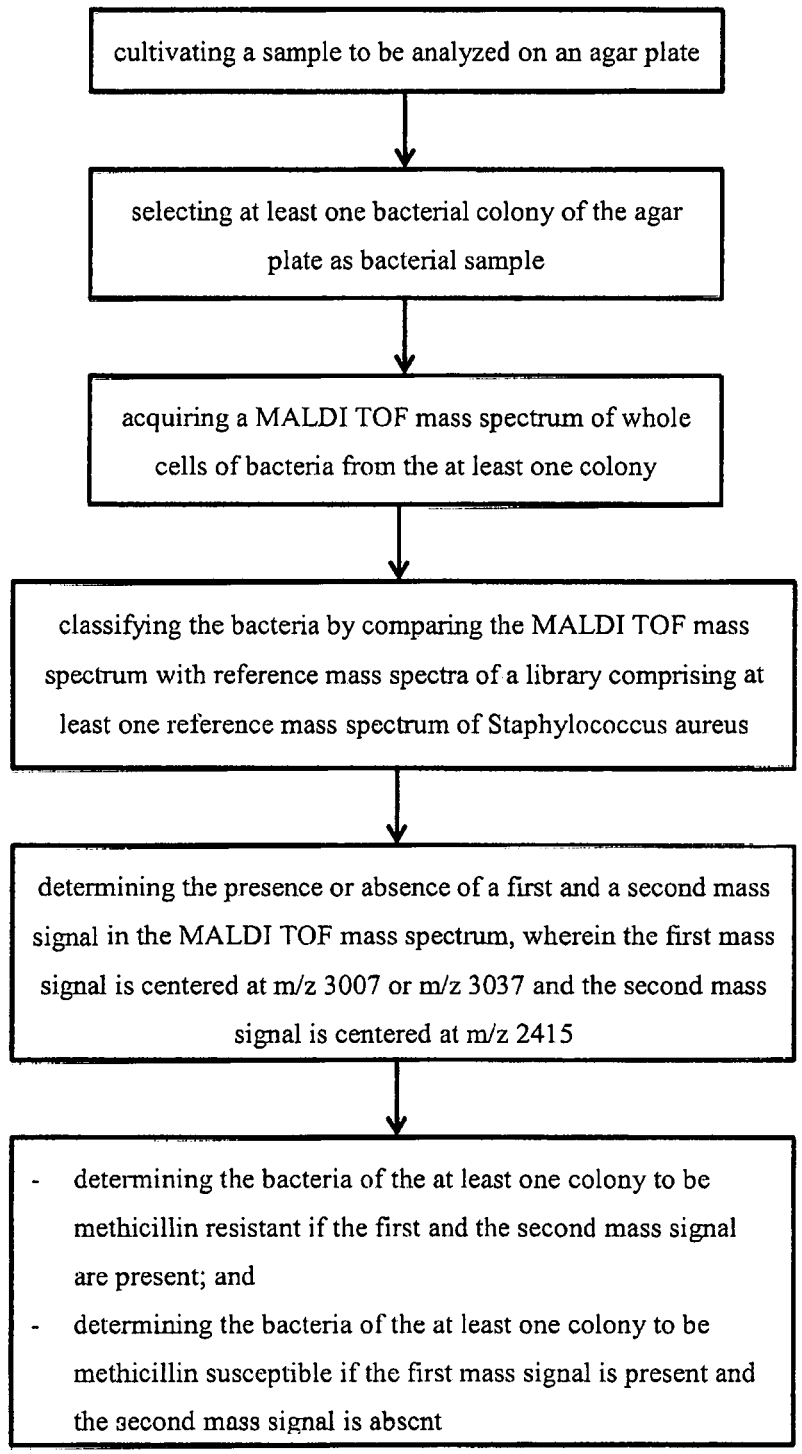
FIG. 2 shows a flowchart of a preferred method according to the present invention.

FIG. 2 shows a flowchart of a preferred method, comprising the steps: (a) cultivating a sample to be analyzed on an agar plate; (b) selecting at least one bacterial colony of the agar plate as bacterial sample; (c) acquiring a MALDI TOF mass spectrum of whole cells of bacteria from the at least one colony; (d) classifying the bacteria by comparing the MALDI TOF mass spectrum with reference mass spectra of a library comprising at least one reference mass spectrum of *Staphylococcus aureus*; and (e) determining the presence or absence of a first and a second mass signal in the MALDI TOF mass spectrum, wherein the first mass signal is centered at m/z 3007 or m/z 3037 and the second mass signal is centered at m/z 2415, wherein the bacteria of the at least one colony are identified as methicillin resistant when the first and the second mass signal are present and wherein the bacteria of the at least one colony are identified as methicillin susceptible when the first mass signal is present and the second mass signal is absent.

As the necessary data for the detection of a major subgroup of MRS can be obtained during taxonomic species identification of *Staphylococcus aureus* in many clinical laboratories, an analysis of bacterial sample mass spectra according to the present invention might lead to an earlier detection of at least a part of the nosocomial MRSA strains and an earlier isolation of hospitalized patients.

The invention claimed is:

1. A method for identifying methicillin resistant *Staphylococcus aureus* (MRSA) in a bacterial sample comprising the steps:
    directly depositing whole bacteria cells on a MALDI time of flight (MALDI-TOF) mass spectrometer target plate without prior extraction,
    acquiring a MALDI-TOF mass spectrum of the whole bacteria,
    classifying bacteria in the sample as *Staphylococcus aureus* (SA) by comparing the MALDI-TOF mass spectrum with reference mass spectra of a library comprising at least one reference mass spectrum of *Staphylococcus aureus*,
    determining the presence or absence of a first mass signal in the MALDI-TOF mass spectrum centered at m/z 3007 or m/z 3037;
    determining the presence or absence of a second mass signal in the MALDI-TOF mass spectrum centered at m/z 2415, wherein the presence or absence of a formylated version of the phenol soluble modulin peptide (PSM-mec) is determined by the presence or absence of the second mass signal, and
    indicating the bacteria of the bacterial sample to be methicillin resistant if the first and the second mass signals are present, and to be undetermined with regard to methicillin resistance and with regard to methicillin susceptibility if the first mass signal is absent.

2. The method according to claim 1 wherein the bacterial sample stems from one of an agar plate, liquid nutrient broth, a smear, a body fluid and a blood culture.

3. The method according to claim 1 wherein an additional antibiotic susceptibility test is performed after determining the presence of the formylated version of the PSM-mec peptide in order to confirm the identification of methicillin resistant *Staphylococcus aureus*.

4. The method according to claim 1, wherein the whole bacterial cells are smeared onto a target plate and overlaid directly with a MALDI matrix.

5. The method according to claim 1, wherein the whole bacterial cells are deposited on a target plate, extracted with formic acid/acetonitrile and overlaid with a MALDI matrix.

6. The method according to claim 5, wherein the formic acid (70%) is added, followed by acetonitrile, and then mixed and air dried.

7. The method according to claim 6, where the MALDI matrix is α-cyano-4-hydroxycinnamic acid.

* * * * *